US006635624B1

(12) United States Patent
Davis et al.

(10) Patent No.: US 6,635,624 B1
(45) Date of Patent: Oct. 21, 2003

(54) NUCLEOTIDE VECTOR COMPOSITION CONTAINING SUCH VECTOR AND VACCINE FOR IMMUNIZATION AGAINST HEPATITIS

(75) Inventors: Heather Lynn Davis, Ottawa (CA); Robert Gerald Whalen, Paris (FR); Marie-Louise Michel, Paris (FR)

(73) Assignees: Institut Pasteur, Paris (FR); Institut National de la Sant et de la Recherche Medical, Paris (FR); Universite d'Ottawa, Ottawa (CA)

(*) Notice: Subject to any disclaimer, the term of this patent is extended or adjusted under 35 U.S.C. 154(b) by 0 days.

(21) Appl. No.: 09/146,072

(22) Filed: Sep. 2, 1998

Related U.S. Application Data

(63) Continuation of application No. 08/633,821, filed on Aug. 2, 1996, now abandoned.

(30) Foreign Application Priority Data

Oct. 22, 1993 (FR) .............................. 93 12659
Apr. 27, 1994 (WO) ................... PCT/FR94/00483

(51) Int. Cl.$^7$ .................. A01N 43/04; A61K 31/70; C12N 15/63; C12N 15/70; C12N 15/74

(52) U.S. Cl. ...................... 514/44; 435/320.1

(58) Field of Search .................... 514/44; 435/320.1

(56) References Cited

U.S. PATENT DOCUMENTS

| | | | |
|---|---|---|---|
| 5,256,553 A | 10/1993 | Overell et al. | 435/456 |
| 5,256,767 A | 10/1993 | Salk et al. | 424/208.1 |
| 5,565,203 A | 10/1996 | Glück et al. | 424/226.1 |
| 5,593,972 A | 1/1997 | Weiner et al. | 514/44 |
| 5,620,896 A | 4/1997 | Herrmann et al. | 435/320.1 |
| 5,643,578 A | 7/1997 | Robinson et al. | 424/210.1 |
| 5,679,647 A | 10/1997 | Carson et al. | 514/44 |
| 5,714,316 A | 2/1998 | Weiner et al. | 435/6 |
| 5,736,524 A | 4/1998 | Content et al. | 514/44 |
| 5,780,448 A | 7/1998 | Davis | 514/44 |
| 5,804,566 A | 9/1998 | Carson et al. | 514/44 |
| 5,814,617 A | 9/1998 | Hoffman et al. | 514/44 |
| 5,830,877 A | 11/1998 | Carson et al. | 514/44 |
| 5,856,462 A | 1/1999 | Agrawal | 536/24.5 |
| 5,972,346 A | 10/1999 | Hauser et al. | 424/227.1 |
| 5,981,274 A | 11/1999 | Tyrrell et al. | 435/320.1 |
| 5,985,847 A | 11/1999 | Carson et al. | 514/44 |

FOREIGN PATENT DOCUMENTS

| | | |
|---|---|---|
| CA | 1 169 793 | 6/1984 |
| WO | WO 88/06185 | 8/1988 |
| WO | WO 90/11092 A1 | 10/1990 |
| WO | WO92/06212 | 4/1992 |
| WO | WO 93/15207 | 8/1993 |
| WO | WO 95/05853 A1 | 3/1995 |

OTHER PUBLICATIONS

Kuby, J. (1994) Immunology, 2$^{nd}$ Ed., W.H. Freeman and Company, New York, pp. 473–474.*

Chattergoon et al. Genetic Immunization: A New Era in Vaccines and Immune Therapeutics. FASEB Journal, vol. 11, pp. 753–763, Aug. 1997.*

Zelphati, O., et al., Inhibition of HIV–1 Replication in Cultured Cells with Antisense Oligonucleotides Encapsulated in Immunoliposomes, *Antisense Research and Development,* 3:323–338, (1993).

Milich et al. (1986).

Shih et al. (1993).

Haynes et al. (1993).

Szmuness et al. (1982).

Böhm et al. (1996).

Jones, T., et al., "Synthetic oligodeoxynucleotiedes containing CpG motifs enhance immunogenicity of a peptide malaria vaccine in Aotus monkeys", *Vaccine,* 17:3065–3071, (1999).

Karlin, S., et al., "Why is CpG Suppressed in the Genomes of Virtually All Small Eukaryotic Viruses but Not in Those of large Eukaryotic Virues?", Journal of Virology, 2889–2897, (1994).

Kataoka, T., et al., "Antitumor Activity of Synthetic Oligonucleotides with Sequences from cDNA Encoding Proteins of *Mycbacterium vobis* BCG", Jpn. J. Cancer Res., 83:244–247, (1992).

Krieg, A., et al., "CpG motifs in bacterial DNA trigger direct B–cell activation", Nature, 374:546–549, (1995).

Li, Z., et al., "Desmin sequence elements regulating skeletal muscle–specific expression in transgenic mice", *Development,* 117:947–959, (1993).

Liu, H., et al., "Immunostimulatory CpG Oligodeoxynucleotides Enhance the Immune Response to Vaccine Strategies Involving Granulocyte–Machrophate colony–Stimulating Factor", Blood, 92:3730–3736, (1998).

McIntyre, K., et al., "A Sense Phosphorothioate Oligonucleotide Directed to the Initiation Codon of Transcription Factor NF–kB p65 Causes Sequence–Specific Immune Stimulation", *Antisense&Nucleic Acid Drug Development,* 3:309–322, (1993).

Manzel, L., et al., "Lack of Immune Stimulation by Immobilized CpG–Oligodeoxynucleotide", *Antisense&Nucleic Acid Drug Development,* 9:459–464, (1999).

(List continued on next page.)

Primary Examiner—Anne-Marie Falk
(74) Attorney, Agent, or Firm—Wolf, Greenfield & Sacks, P.C.

(57) ABSTRACT

The invention relates to methods of inducing an immunogenic response in a subject that include administering a nucleotide plasmid vector that includes a gene coding for a surface antigen protein derived from hepatitis B virus and a promoter for the expression of the gene. The invention also relates to vaccine compositions for protecting against hepatitis B virus.

28 Claims, 12 Drawing Sheets

OTHER PUBLICATIONS

Mojcik, C., et al., "Administration of a Phosphorothioate Oligonucleotide Antisense Murine Endogenous Retroviral MCF env Causes Immune Effects in Vivo in a Sequence–Specific Manner", *Clinical Immunology and ImmunoPathology*, 67:2:130–136, (1993).

Pisetsky, D., et al., "Immunologic Consequences of Nucleic Acid Therapy", *Antisense&Nucleic Acid Drug Development*, 5:219–225, (1995).

Prince, A., et al., "Successful nucleic acid based immunization of newborn chimpanzees against hepatitis B virus", *Vaccine*, 15:916–919, (1997).

Raz, E.,et al., "Intradermal gene immunization: The possible role of DNA utake in the induction of cellular immunity to viruses", *Proc. Natl. Acad. Sci.*, 91:9515–9523, (1994).

Robinson, H., "Nucleic acid vaccines: an overview", *Vaccine*, 15:8:785–787, (1997).

Sands, H., et al., "Biodistribution and Metabolism of Internally 3H–Labeled Oligonucleotides. I. Comparison of a Phosphodiester and a Phosphorothioate", *The American Society for Pharmacology*, 45:932–943, (1994).

Stein, C., et al., "Antisense Oligonucleotides as Therapeutic Agents—Is the bullet Really Magical", *Science*, 261:1004–1012, (1993).

Thomsen, D., et al., "Promoter–regulatory region of the major immediate early gene of human cytomegalovirus", *Proc. Natl. Acad. Sci.*, 81:659–663, (1984).

Tokunaga, T., et al., "Antitumor Activity of Deoxyribonucleic Acid Fraction From *Mycobacterium bovis* BCG. I. Isolation, Physicochemical Characterization, and Antitumor Activity", *JNCI*, 72:955–962, (1984).

Ulmer, J., et al., "Heterologous protection Against Influenza by Injection of DNA Encoding a Viral Protein", *Science*, 259:1745–1749, (1993).

Valenzuela, P., et al., "Synthesis and assembly of hepatitis B virus surface antigen particles in yeast", *Nature*, 298:347–350, (1982).

Wang, B., et al., "Gene inoculation generates immune responses against human immunodeficiency virus type 1", *Proc Natl. Acad. Sci.*, 90:4156–4160, (1993).

Yaswen, P., et al., "Effects of Sequences of Thioated Oligonucleotides on cultured Human Mammary Epithelial Cells", *Antisense Research and Development*, 3:67–77, (1993).

Agrawal, S., et al., "Pharmacokinetics of Antisense Oligonucleotides", *Clin Pharmacokinet.*, 7–16, (1995).

Cattaneo, R., et al., "Signals regulating hepatitis B surface antigen transcription", *Nature*, 305:336–338, (1983).

Cowdery, J., et al., Bacterial DNA Induces NK Cells to Produce IFN–γ In Vivo and Increases the Toxicity of Lipopolysaccharides, *Bacterial DNA . . .* , (1996).

Davis, H.,et al., DNA vaccine for hepatitis B: Evidence for immunogenicity in chimpanzees and comparison with other vaccines, *Proc Natl Acad, Sci*, 93:7213–7218, (1996).

Fujieda, S., et al., "Effect of OK–432 on Cytotoxic Activity in Cancer patients without Tumor Burden", *Anticancer Research*, 12:1941–1946, (1992).

Fuller, D., et al., "Induction of immunodeficiency virus–specific immune responses in rhesus monkeys following gene Gun–mediated DNA vaccination", *J. Med. Primates*, 25:236–241, (1996).

Fynan, E., et al., "DNA vaccines: Protective immunizations by parentaeral, mucosal, and gene–gun inoculations", *Proc. Natl. Acad. Sci.*, 90:11478–11482, (1993).

Gao, W., et al., "Phosphorothioate Oligonucleotides are inhibitors of human DNA polymerases and Rnase H: implications for antisense technology", 223–229, (1991).

Davis, H.,et al., "Direct gene transfer into skeletal muscle in vivo: Factors affecting efficiency of transfer and stability of expression" *Human Gene Therapy*, 4: 151–159, (1993).

Davis, H.,et al., "DNA–based immunization induces continuous secretion of hepatitis B surface antigen and high levels of circulating antibod" *Human Molecular Genetics*, 2:1847–1852, (1993).

Lutynski R and Juszczyk R, "The level of anti–HBs in blood serum of persons selected from a group of Krakow inhabitants" *Folia Med. Cracov.*, 38: 63–68, (1997) Abstract.

Whalen, R., et al., DNA Vaccines for Emerging Infectious Diseases: What if?, "Emerging Infectious Diseases", (1996), 2:3:168–175.

Calandra G.B. et al., Recommendations for Prevention of Hepatitis B with Vaccine, Hepatitis B Vaccines in Clinical Practice, Merck Research Laboratories, pp. 1–16, 1993.

Chambon, P., ADN: sur la piste du vaccine génétique, *Sciences et Avenir*, Sep. 1993, pp. 22–25.

Fujisawa, T. et al., Serial changes in titers of antibody to hepatitis B surface antigen after immunization of infants born to mothers with hepatitis B e antigen., *J Pediatr Gastroenterol Nutr*, Oct. 1996, 23(3):270–4.

Hayes, J.R. et al., Particle–mediated nucleic acid immunization, Journal of Biotechnology 44, 1996, pp. 37–42.

Kuhöber, A., et al. DNA Immunization Induces Antibody and Cytotoxic T Cell Responses to Hepatitis B Core Antigen in H–$2^b$ Mice, *The American Association of Immunologists*, 1996, pp. 3687–3695.

LeBorgne, S. et al., In Vivo Induction of Specific Cytotoxic T Lymphocytes in Mice and Rhesus Macaques Immunized with DNA Vector Encoding an HIV Epitope Fused with Hepatitis B Surface Antigen, *Virology* 240, 304–315, 1998, Article No. VY978942.

Lee, P.I. et al., Long–term efficacy of recombinant hepatitis B vaccine and risk of natural infection in infants born to mothers with hepatitis B e antigen, *J Pediatr*, May 1995, 126(5 Pt 1):716–21.

Wolff et al., Direct Gene Transfer into Muse Muscle in Vivo, Science, vol. 247, Mar. 1990, pp. 1465–1468.

Raz, E. et al., "Systemic immunological effects of cytokine genes injected into skeletal muscle", *Proc. Natl. Acad. Sci. USA*, May 1993, pp. 4523–4527, vol. 90.

Tang, D. et al., "Genetic immunization is a simple method for eliciting an immune response", *Nature*, Mar. 12, 1992, pp. 152–154, vol. 356.

* cited by examiner

SEQUENCE LISTING

<160> NUMBER OF SEQ ID NOS: 1

<210> SEQ ID NO 1
<211> LENGTH: 5618
<212> TYPE: DNA
<213> ORGANISM: Artificial
<220> FEATURE:
<223> OTHER INFORMATION: Synthetic Sequence

<400> SEQUENCE: 1

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
```

-continued

| | |
|---|---|
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttaact ggcttatcga aattaatacg actcactata gggagaccca agcttggtac | 900 |
| cgggccccc ctcgaggatt ggggaccctg cgctgaacat ggagaacatc acatcaggat | 960 |
| tcctaggacc ccttctcgtg ttacaggcgg ggttttcttt gttgacaaga atcctcacaa | 1020 |
| taccgcagag tctagactcg tggtggactt ctctcaattt tctaggggga actaccgtgt | 1080 |
| gtcttggcca aaattcgcag tccccaacct ccaatcactc accaacctct tgtcctccaa | 1140 |
| cttgtcctgg ttatcgctgg atgtgtctgc ggcgttttat catcttcctc ttcatcctgc | 1200 |
| tgctatgcct catcttcttg ttggttcttc tggactatca aggtatgttg cccgtttgtc | 1260 |
| ctctaattcc aggatcctca acaaccagca cgggaccatg ccggacctgc atgactactg | 1320 |
| ctcaaggaac ctctatgtat ccctcctgtt gctgtaccaa accttcggac ggaaattgca | 1380 |
| cctgtattcc catcccatca tcctgggctt tcggaaaatt cctatgggag tgggcctcag | 1440 |
| cccgtttctc ctggctcagt ttactagtgc catttgttca gtggttcgta gggctttccc | 1500 |
| ccactgtttg gctttcagtt atatggatga tgtggtattg ggggccaagt ctgtacagca | 1560 |
| tcttgagtcc cttttaccg ctgttaccaa ttttctttg tctttgggta tacatttaaa | 1620 |
| ccctaacaaa acaagagat ggggttactc tctaaatttt atgggttatg tcattggatg | 1680 |
| ttatgggtcc ttgccacaag aacacatcat acaaaaaatc aaagaatgtt ttagaaaact | 1740 |
| tcctattaac aggcctattg attgaaaagt atgtcaacga attgtgggtc ttttgggttt | 1800 |
| tgctgcccct tttacacaat gtggttatcc tgcgttgatg cctttgtatg catgtattca | 1860 |
| atctaagcag gctttcactt tctcgccaac ttacaaggcc tttctgtgta acaatacct | 1920 |
| gaacctttac cccgttgccc ggcaacggcc aggtctgtgc caagtgtttg ctgacgcaac | 1980 |
| ccccactggc tggggcttgg tcatgggcca tcagcgcatg cgtggaacct tttcggctcc | 2040 |
| tctgccgatc catactgcgg aactcctagc cgcttgtttt gctcgcagca ggtctggagc | 2100 |
| aaacattatc gggactgata actctgttgt cctatcccgc aaatatacat cgtttccatg | 2160 |
| gctgctaggc tgtgctgcca actggatcct gcgcgggacg tcctttgttt acgtcccgtc | 2220 |
| ggcgctgaat cctgcggacg acccttctcg gggtcgcttg ggactctctc gtccccttct | 2280 |
| ccgtctgccg ttccgaccga ccacggggcg cacctctctt tacgcggact ccccgtctgt | 2340 |
| gccttctcat ctgccggacc gtgtgcactt cgcttcacct ctgcacgtcg catggagacc | 2400 |
| accgtgaacg cccaccaaat attgcccaag gtcttacata agaggactct ggactctca | 2460 |
| gcaatgtcaa cgaccgacct tgaggcatac ttcaaagact gtttgtttaa agactgggag | 2520 |
| gagttggggg aggagattag gttaaaggtc tttgtactag gaggctgtag gcataaattg | 2580 |
| gtctgcgcac cagcaccatg caacttttc acctctgcct aatcatctct tgttcatgtc | 2640 |
| ctactgttca agcctccaag ctgtgccttg ggtggctttg gggcatggac atcgacccttt | 2700 |
| ataaagaatt tggagctact gtggagttac tctcgttttt gccttctgac ttctttcctt | 2760 |
| cagtacgaga tctggccagg atccactagt tctagagcgg ccgccaccgc ggtggagctc | 2820 |
| cagcttttgt tccctttagt gagggttaat tgcgcgcatg cccgacggcg aggatctcgt | 2880 |
| cgtgacccat ggcgatgcct gcttgccgaa tatcatggtg aaaatggcc gcttttctgg | 2940 |
| attcatcgac tgtggccggc tgggtgtggc ggaccgctat caggacatag cgttggctac | 3000 |
| ccgtgatatt gctgaagagc ttggcggcga atgggctgac cgcttcctcg tgctttacgg | 3060 |

```
tatcgccgct cccgattcgc agcgcatcgc cttctatcgc cttcttgacg agttcttctg   3120
agcgggactc tggggttcga aatgaccgac caagcgacgc ccaacctgcc atcacgagat   3180
ttcgattcca ccgccgcctt ctatgaaagg ttgggcttcg gaatcgtttt ccgggacgcc   3240
ggctggatga tcctccagcg cggggatctc atgctggagt tcttcgccca ccccaacttg   3300
tttattgcag cttataatgg ttacaaataa agcaatagca tcacaaattt cacaaataaa   3360
gcattttttt cactgcattc tagttgtggt ttgtccaaac tcatcaatgt atcttatcat   3420
gtctggatcc cgtcgacctc gagagcttgg cgtaatcatg gtcatagctg tttcctgtgt   3480
gaaattgtta tccgctcaca attccacaca acatacgagc cggaagcata agtgtaaag    3540 cctggggtgc ctaatgagtg agctaactca cattaattgc gttgcgctca ctgcccgctt   3600
tccagtcggg aaacctgtcg tgccagctgc attaatgaat cggccaacgc gcggggagag   3660
gcggtttgcg tattgggcgc tcttccgctt cctcgctcac tgactcgctg cgctcggtcg   3720
ttcggctgcg gcgagcggta tcagctcact caaaggcggt aatacggtta ccacagaat    3780 cagggqataa cgcaggaaag aacatgtgag caaaaggcca gcaaaaggcc aggaaccgta   3840
aaaaggccgc gttgctggcg tttttccata ggctccgccc cctgacgag catcacaaaa     3900 atcgacgctc aagtcagagg tggcgaaacc cgacaggact ataaagatac caggcgtttc   3960
cccctggaag ctccctcgtg cgctctcctg ttccgaccct gccgcttacc ggatacctgt   4020
ccgcctttct cccttcggga agcgtggcgc tttctcaatg ctcacgctgt aggtatctca   4080
gttcggtgta ggtcgttcgc tccaagctgg gctgtgtgca cgaaccccc gttcagcccg     4140 accgctgcgc cttatccggt aactatcgtc ttgagtccaa cccggtaaga cacgacttat   4200
cgccactggc agcagccact ggtaacagga ttagcagagc gaggtatgta ggcggtgcta   4260
cagagttctt gaagtggtgg cctaactacg gctacactag aaggacagta tttggtatct   4320
gcgctctgct gaagccagtt accttcggaa aaagagttgg tagctcttga tccggcaaac   4380
aaaccaccgc tggtagcggt ggtttttttg tttgcaagca gcagattacg cgcagaaaaa   4440
aaggatctca agaagatcct ttgatctttt ctacgggtc tgacgctcag tggaacgaaa     4500
actcacgtta agggattttg gtcatgagat tatcaaaaag gatcttcacc tagatccttt   4560
taaattaaaa atgaagtttt aaatcaatct aaagtatata tgagtaaact ggtctgaca    4620 gttaccaatg cttaatcagt gaggcaccta tttcagcgat ctgtctattt cgttcatcca   4680
tagttgcctg actccccgtc gtgtagataa ctacgatacg ggagggctta ccatctggcc   4740
ccagtgctgc aatgataccg cgagacccac gctcaccggc tccagattta tcagcaataa   4800
accagccagc cggaagggcc gagcgcagaa gtggtcctgc aactttatcc gcctccatcc   4860
agtctattaa ttgttgccgg gaagctagag taagtagttc gccagttaat agtttgcgca   4920
acgttgttgc cattgctaca ggcatcgtgg tgtcacgctc gtcgtttggt atggcttcat   4980
tcagctccgg ttcccaacga tcaaggcgag ttacatgatc ccccatgttg tgcaaaaaag   5040
cggttagctc cttcggtcct ccgatcgttg tcagaagtaa gttggccgca gtgttatcac   5100
tcatggttat ggcagcactg cataattctc ttactgtcat gccatccgta agatgctttt   5160
ctgtgactgg tgagtactca accaagtcat tctgagaata gtgtatgcgg cgaccgagtt   5220
gctcttgccc ggcgtcaata cgggataata ccgcgccaca tagcagaact ttaaaagtgc   5280
tcatcattgg aaaacgttct cggggcgaa aactctcaag gatcttaccg ctgttgagat    5340
ccagttcgat gtaacccact cgtgcaccca actgatcttc agcatctttt actttcacca   5400
```

-continued

| | |
|---|---|
| gcgtttctgg gtgagcaaaa acaggaaggc aaaatgccgc aaaaaaggga ataagggcga | 5460 |
| cacggaaatg ttgaatactc atactcttcc tttttcaata ttattgaagc atttatcagg | 5520 |
| gttattgtct catgagcgga tacatatttg aatgtattta gaaaaataaa caaatagggg | 5580 |
| ttccgcgcac atttccccga aaagtgccac ctgacgtc | 5618 |

NUCLEOTIDE VECTOR COMPOSITION CONTAINING SUCH VECTOR AND VACCINE FOR IMMUNIZATION AGAINST HEPATITIS

This is a continuation of application Ser. No. 08/633,821, filed Aug. 2, 1996, now abandoned, which is incorporated herein by reference.

BACKGROUND OF THE INVENTION

The present application relates to a vector for immunization against hepatitis.

It is also related to a composition containing this vector.

Immunization by injection of bare DNA into muscle tissues has been the object of several studies since the beginning of the 1990s.

Thus, ULMER et al. (Science, 259, 1745–1749, 1993) obtained protection against the Influenza virus by induction of the cytotoxic T lymphocytes through injection of a plasmid coding for the Influenza A nucleoprotein into the quadriceps of mice. The plasmid used carries either the Rous sarcoma virus promoter or the cytomegalo virus promoter.

RAZ et al. (Proc. Natl. Acad. Sci. USA, 90, 4523–4527, 1993) injected vectors comprising the Rous sarcoma virus promoter and a gene coding for interleukin-2, interleukin-4 or the $\beta$1-type transforming growth factor (TGF-$\beta$1). The humoral and cell immune responses of the mice to which these plasmids have been intramuscularly administered are improved.

WANG et al. (Proc. Natl. Acad. Sci. USA, 90, 4156–4160, 1993) injected a plasmid carrying a gene coding for the envelope protein of the HIV-1 virus into mice muscles. The plasmid injection was preceded by treatment with bupivacaine in the same area of the muscle. The authors demonstrate the presence of antibodies capable of neutralizing the HIV-1 virus infection. However, it will be noted that DNA was injected twice a week for a total of four injections.

DAVIS et al. (Compte-Rendu du 28ème Congrès Européen sur le muscle, Bielefeld, Germany, 21–25 September 1992) injected plasmids carrying a luciferase or $\beta$-galactosidase gene coding by pretreating the muscles with sucrose or a cardiotoxin. The authors observed the expression of luciferase or $\beta$-galactosidase.

More recently, an article published in Science et Avenir (September 1993, pages 22–25) indicates that WHALEN et DAVIS succeeded in immunizing mice against the hepatitis B virus by injecting pure DNA from the virus into their muscles. An initial injection of snake venom toxin, followed 5 to 10 days later by a DNA injection, is generally cited. It is specified that this is not a practical method.

These studies were preceded by other experiments in which various DNAs were injected, in particular into muscle tissues. Thus, the PCT/US application No. 90/01 515 (published under No. WO-90/11 092) discloses various plasmid constructions which can be injected in particular into muscle tissues for the treatment of muscular dystrophy. However, this document specifies that DNA is preferentially injected in liposomes.

This also applies to Canadian patent CA-362.966 (published under No. 1.169.793) which discloses the intramuscular injection of liposomes containing DNA coding in particular for HBs and HBc antigens. The results described in this patent mention the HBs antigen expression. The presence of anti-HBs antibodies was not investigated.

International application PCT/FR 92/00 898 (published under No. WO-93/06 223) discloses viral vectors which can be conveyed to target cells by blood. These vectors are thus recognized by the cell receptors, such as the muscle cells, and can be used in the treatment of muscular dystrophy or of thrombosis.

This application does not relate to immunization against viruses such as, for example, that of hepatitis B.

Thus, it arises from the state of the art cited that although immunization techniques against hepatitis by injection of bare DNA are already known, these techniques had many disadvantages which made their implementation impractical.

Furthermore, the bare DNA used to vaccinate the mice was pure DNA from the virus. This type of treatment can not be considered for human vaccination due to the risks involved for the patients.

Finally, the earliest experiments in which the injected DNA is contained in liposomes did not demonstrate any immune response.

The applicant has therefore aimed at discovering new vector constructions allowing immunization against hepatitis without having a detrimental effect on human health.

He has further aimed at finding an additive for compositions containing the constructions which would allow an effective degeneration of muscle tissue before the DNA injection, and compatible with the requirements of human health.

The applicant has surprisingly shown that it is possible to achieve an effective and durable level of antibodies much greater than the level permitting to obtain in man an efficient and durable immune protection against infection by the hepatitis virus, by administering by intramuscular injection a vector with defined construction, and a substance capable of inducing a coagulating necrosis of the muscle fibres.

The present application thus relates to a nucleotide vector comprising at least:
  a gene or a complementary DNA coding for at least a part of the virus protein, and
  a promoter allowing the expression of this gene in muscle cells.

Said vector may not replicate in these cells.

It may also be replicative, allowing to obtain a high number of copies per cell and to enhance the immune response.

The vector is also chosen in order to avoid its integration into the cell's DNA, such integrations being known to activate the oncogens and induce cell canceration.

The vector according to the present invention is advantageously a plasmid of partly bacterial origin and notably carrying a bacterial replication origin and a gene allowing its selection, such as a gene for resistance to an antibiotic.

This vector may also be provided with a replication origin allowing it to replicate in the muscle cells of its host, such as the replication origin of the bovine papilloma virus.

The gene or the complementary DNA included in this vector advantageously codes for a structure protein of a virus but it can also code for a regulatory protein.

The gene or complementary DNA carried by this vector can code for a least a portion of a hepatitis virus protein, in particular hepatitis B, and preferentially the protein HBs, in one of its forms S, S-preS2 or S-preS2-preS1, in which case the gene is gene S.

The virus may also be responsible for another hepatitis such as a hepatitis A or of a non-A, non-B hepatitis, such as a hepatitis C, E or delta.

The gene or protein sequences for these hepatitis viruses are described or may be deduced from the following documents:
  patent FR-79 21 811, patent FR 80.09.039,
  patent EP-81.400.634, patent FR 84.03.564,
  patent EP 91.830.479 and the article by Najarian et al. (Proc. Natl. Acad. Sci. USA, 1985, 82, 2627–2631).

The vector may also include genes coding for at least a portion of the gp160 protein of HIV-1 virus associated with the p25 protein, and/or the p55 protein, and/or the p18 protein or at least a gene coding for the Rev protein of HIV-1 virus.

The vector may also include instead of a virus protein, a protein from a pathogenic micro-organism such as a protein from the bacterium causing diphtheria, whooping cough, listeriosis, the tetanus toxin etc.

The promoter carried by this vector is advantageously the promoter for the cytomegalovirus (CMV). It may however be any other promoter which allows the efficient expression of the gene in the muscle cells.

It may thus be:
- an internal or endogenic promoter, that is a promoter of the virus from which the gene is taken; such a promoter may be completed by a regulatory element of the muscle or another tissue, in particular an activating element,
- a promoter from a gene of a cytoskeleton protein, in particular desmine as described by BOLMONT et al. (Journal of submicroscopic cytology and pathology, 1990, 22, 117–122) et ZHENLIN et al. (Gene, 1989, 78, 243–254).
- the promoter from the virus HBV surface genes.

Generally, the promoter may be heterologous to the host, that is not naturally found in the host, but it is advantageously homologous, while being originally active in a tissue other than the muscle tissue.

In addition to the promoter, the vector may include a terminal transcription sequence, situated downstream of the gene.

Such vector may be the pCMV/HBS or pRCCMV-HBS plasmid, having the SEQ ID No. 1 sequence, filed under No. I-1370 with the Collection Nationale des Cultures des Micro-organismes de l'Institut Pasteur (CNCM) on Oct. 21, 1993.

It may also be the pRSV/HBS plasmid filed under No. I-1371 with the CNCM on Oct. 21, 1993.

This plasmid has a similar structure to pCMV/HBS but includes the Rous sarcoma virus (RSV) promoter instead of the cytomegalovirus (CMV) promoter.

Other plasmids may be:
- pCMVHB-S1.S2.S constructed by inserting the fragment Bgl II-Bgl II of the S gene, obtained from pCP10, into a pBlueScript vector modified to contain supplementary cloning sites in the "polylinker" portion. The fragment containing the S gene was then removed by KpnI-BssH II digestion then cloned into the corresponding sites of pcDNA 3 (In vitrogen, Rad Systems Europe Ltd, Abingdon UK) so as to obtain pCMVHB-S1.S2.S. This plasmid was filed under No. I-1411 with the CNCM.
- pCMVHB-S2.S obtained by eliminating the pre-S1 part of the HBS gene from pCMVHB-S1.S2.S by KpnI/MstI digestion, then by bonding the two extremities after treatment with S1 nuclease. pCMVHB-S2.S was filed with the CNCM under No. I-1410.
- pHBV-S1.S2.S, filed with the CNCM under No. I-1409, was obtained by inserting the S gene Bgl II- Bgl II fragment, obtained from pCP10, into a pBlueScript vector modified to contain supplementary cloning sites in the "polylinker" portion.
- pBS-SKT-S1.S2.S codes for the three envelope proteins S, S-preS$_1$ and S-preS$_1$-preS$_2$ of the HBV virus.

The present invention further relates to nucleotide sequences comprising a promoter homologous to the host and another regulatory sequence for the expression of a gene or complementary DNA coding for one of the above mentioned proteins.

The present invention further relates to a vaccine or medicine containing at least one vector, or a nucleotide sequence, such as defined above.

It further relates to a composition capable of inducing a cytotoxic response comprised of at least one nucleotide sequence expressed in the muscle cells and including a promoter such as defined above.

It further relates to a non-lipid pharmaceutical composition for immunization against a viral infection such as a hepatitis including, on the one hand, at least a substance capable of inducing a coagulating necrosis of the muscle fibres and, on the other hand, a vector such as described above or including one of the nucleotide sequences, complete or partial, such as described above. By partial sequence is meant a sequence coding for at least 6 amino acids.

Said substance is advantageously bupivacaine.

Advantageously, said composition is characterized in that the vector is administered in the muscle of the individual to immunized, at least 5 days after the administration of-the bupivacaine, and substantially in the same location.

Such prior administration of bupivacaine surprisingly allows to increase the effectiveness of the vector administration as well as the immunization of the individual.

Advantageously, the vector is administered ten days after administration of bupivacaine, and substantially in the same location of the individual's muscle.

The present composition may also contain additives which are compatible and pharmaceutically acceptable.

Such composition is preferentially administered by intramuscular injection. The injection can be carried out using a syringe designed for such use or using a liquid jet gun such as described by FURTH et al. (1992, Anal. Biochem. 205, 365–368).

The quantity of bupivacaine required to obtain sufficient degeneration of the muscle tissue, in order to achieve optimal immunization, is in the order of 0.10 mg to 10 mg per dose of injected composition.

The quantity of vector to be injected in order to achieve optimal immunization of the individual against a hepatitis varies according to the protein coded by the gene carried by the vector. As an indication, between 0.1 and 1000 μg of vectors are injected per individual.

The vectors may be obtained by methods known to those skilled in the art, in particular by synthesis or by genetic engineering methods.

Such methods are those described in particular in the technical manual:

Maniatis T. et al. 1982—Molecular Cloning, A Laboratory Manual, Cold Spring Harbour—Ed. New York.

The present invention is illustrated by, without in any way being limited to, the following examples, in which.

EXAMPLE 1

Induction of Antibodies Against a Hepatitis B Surface Antigen by Sequential Injection of Bupivacaine and of a Plasmid Carrying a Gene Coding for the Antigen 1) Materials and Methods 1.1 Bupivacaine pretreatment All experiments were made on the muscles of the anterior tibia (AT) of mice C57BL/6J aged between 5 to 7 weeks.

A single degeneration-regeneration cycle of the muscle fibres is induced in the muscles of the anterior tibia of non-anaesthetized mice, by intramuscular injection of 50 μl marcaine (bupivacaine 0.5%, DMSO 1%) sold by Laboratoires Astra, France. The solution is injected using a tuberculosis syringe with a needle fitted into a polyethylene sleeve, in order to limit the penetration depth to 2 mm.

As marcaine is an anesthetic, injections into the right and left legs were performed at 10 to 30 minute intervals to prevent an overdose.

1.2 DNA preparation

The plasmid used was constructed by cloning into a modified pBlueScript vector of the Xho I-Bgl II restriction fragment of the pCP10 plasmid which contains the gene coding for the HBS surface antigen and the non-translated sequences, both upstream and downstream, including the polyadenylation signal.

The S gene was then recovered by digestion using KpnI-BssHII enzymes and the fragment was cloned into the site of the pRC/CMV vector sold by In Vitrogen. The final plasmid construction was called pCMV-HBS and was filed under No. I-1370 with the CNCM.

Figure 1:
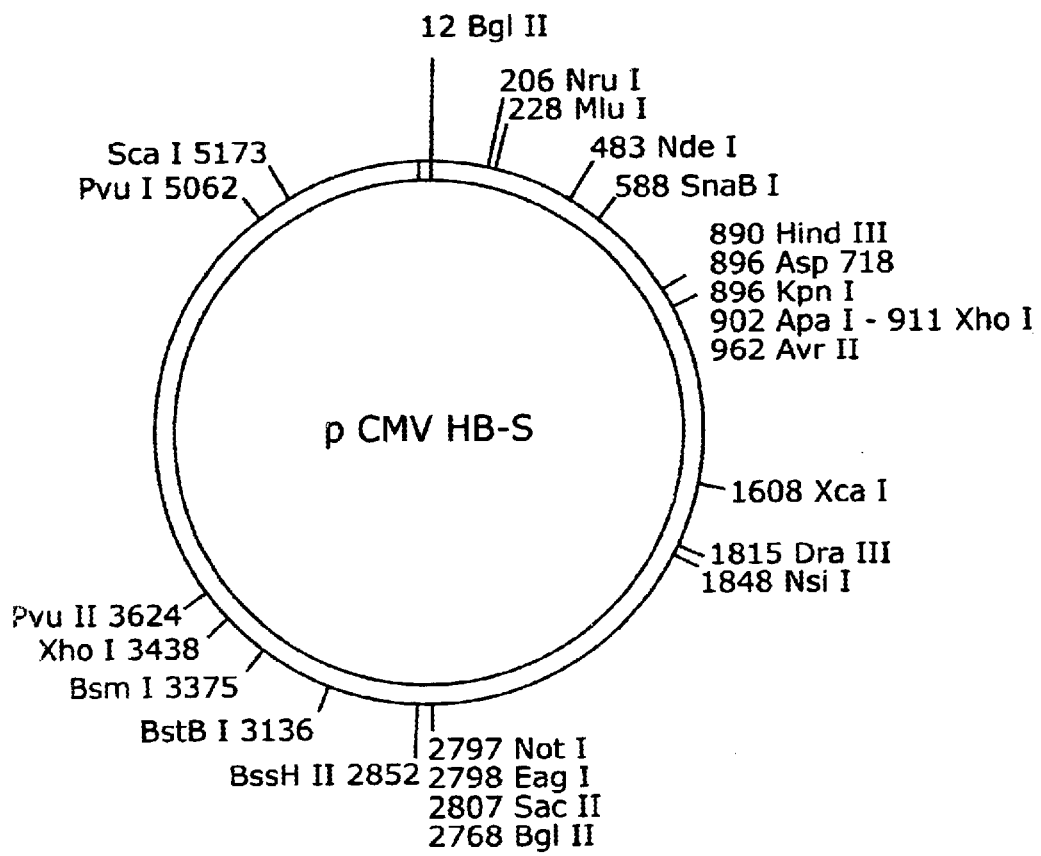
FIG. 1 is a schematic representation of pRC/CMV-HBs plasmid.

This plasmid is represented schematically in FIG. 1. The CMV promoter is situated between the 288 nucleotide which is the cleavage position of MluI and the 896 nucleotide, which is the cleavage position of KpnI. The DNA fragment including the structural gene of the HBs antigen structure was cloned between the 896 and 2852 nucleotides (position of BssH III).

The HBs gene spreads between the 911 (XhoI position) and 2768 nucleotides (Bgl II position) respectively.

The complete sequence for this plasmid is sequence SEQ ID No. 1.

The purified plasmid DNA was prepared by standard methods then redissolved in PBS buffer and stored at −20° C. until the injection was performed.

1.3 DNA injection

One to five days after the marcaine injection, DNA was injected into the same area, the mouse being anaesthetized using sodium pentobarbital (75 mg/kg interperitonal path).

The DNA solution which contains 50 μg of plasmid DNA and 50 μl of PBS buffer was injected by a single intramuscular injection through the skin into the anterior tibia muscles undergoing regeneration.

The injections were performed bilaterally into the two legs of the mice, each animal thus receiving a total of 100 μg of recombinant plasmid DNA. As for the marcaine injection, the DNA solution was injected using the tuberculosis syringe with the needle described previously.

A single intramuscular DNA injection was performed in each leg.

2. Results

The results obtained are summarized in Table I below.

They show very clearly that a DNA injection after treatment with marcaine allows a large number of seric antibodies to be obtained against the hepatitis B surface antigen.

These results are surprising, from the analysis of the state of the art it was not inferred that a plasmid would allow the induction of anti-HBs antibodies which could be found in the serum and thus allow an effective vaccination.

The ease of application of the plasmid vaccination, and the fact that boosters would not be necessary, allows the consideration of a large scale vaccination.

EXAMPLE 2

Comparison of the Efficiency of a Plasmid Injection in the Presence and Absence of Lipids A dose of 10 μg plasmid DNA from the SV40-luciferase vector available commercially ("pGL2-Control Vector" from Promega, reference E1 11) in 50 μl of physiological solution was injected into the sucrose pretreated muscle following the method of David et al. (Hum. Gene Ther. 4:151–159 (1993)). The injected DNA is mixed earlier with lipids such as dioctadecylamidoglycyl spermine (DOGS) or the following mixtures: DOGS+spermidine, and DOGS+polyethyleneglycol (PEG). The luciferase activity was determined 5 days after the injection.

These results are shown in table II below.

They show that the presence of lipids (DOGS) very reduces significantly the efficiency of the plasmid injection with respect to a composition with no lipids (control).

EXAMPLE 3

Figure 2A:
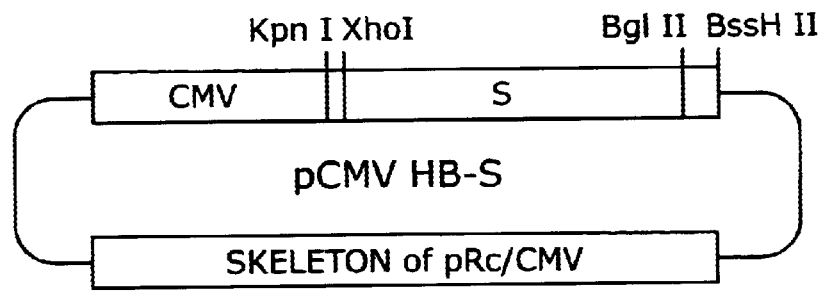
FIGS. 2A to 2D are schematic representations of pCMVHB-S, pCMVHB-S2.S., pCMVHB-S1.S2.S and pHBV-S1.S2.S plasmids, respectively.
Figure 2B:
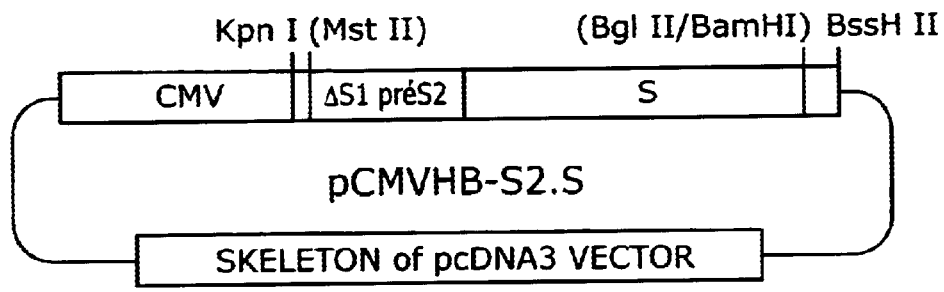
Figure 2C:
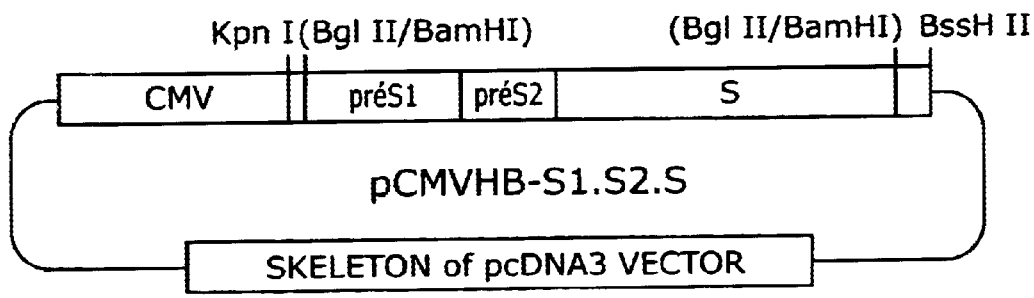
Figure 2D:
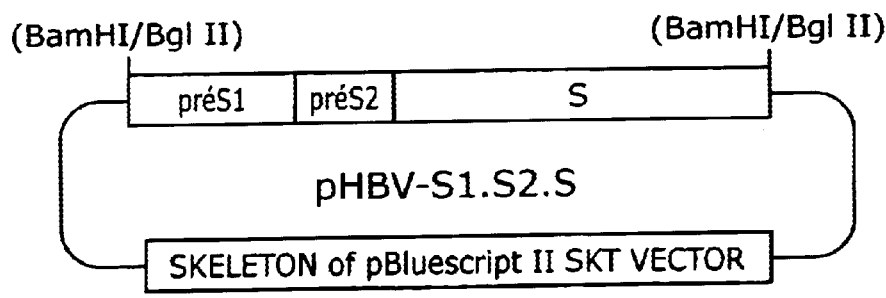
Figure 3:
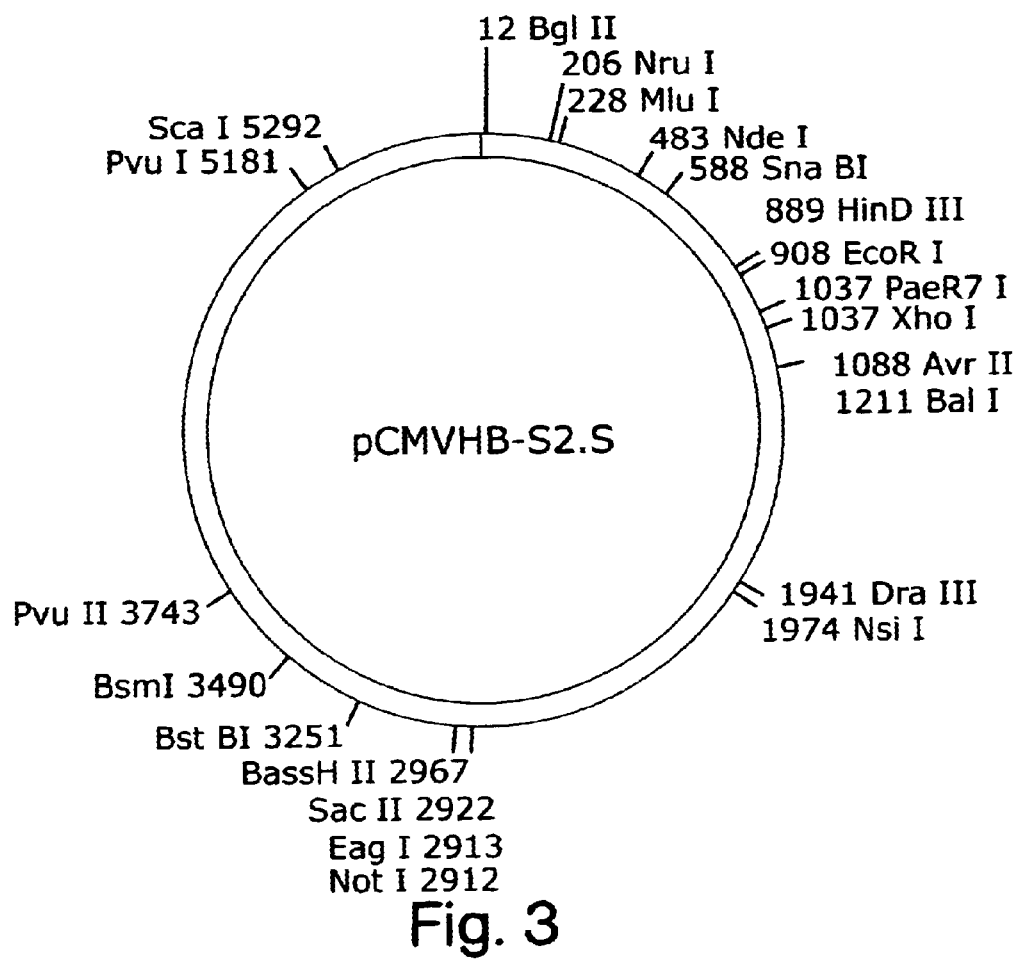
FIGS. 3, 4 and 5 are schematic restriction maps for pCMVHB-S2.S, pCMVHB-S1.S2.S and pRSV-HBS plasmids, respectively.
Figure 4:
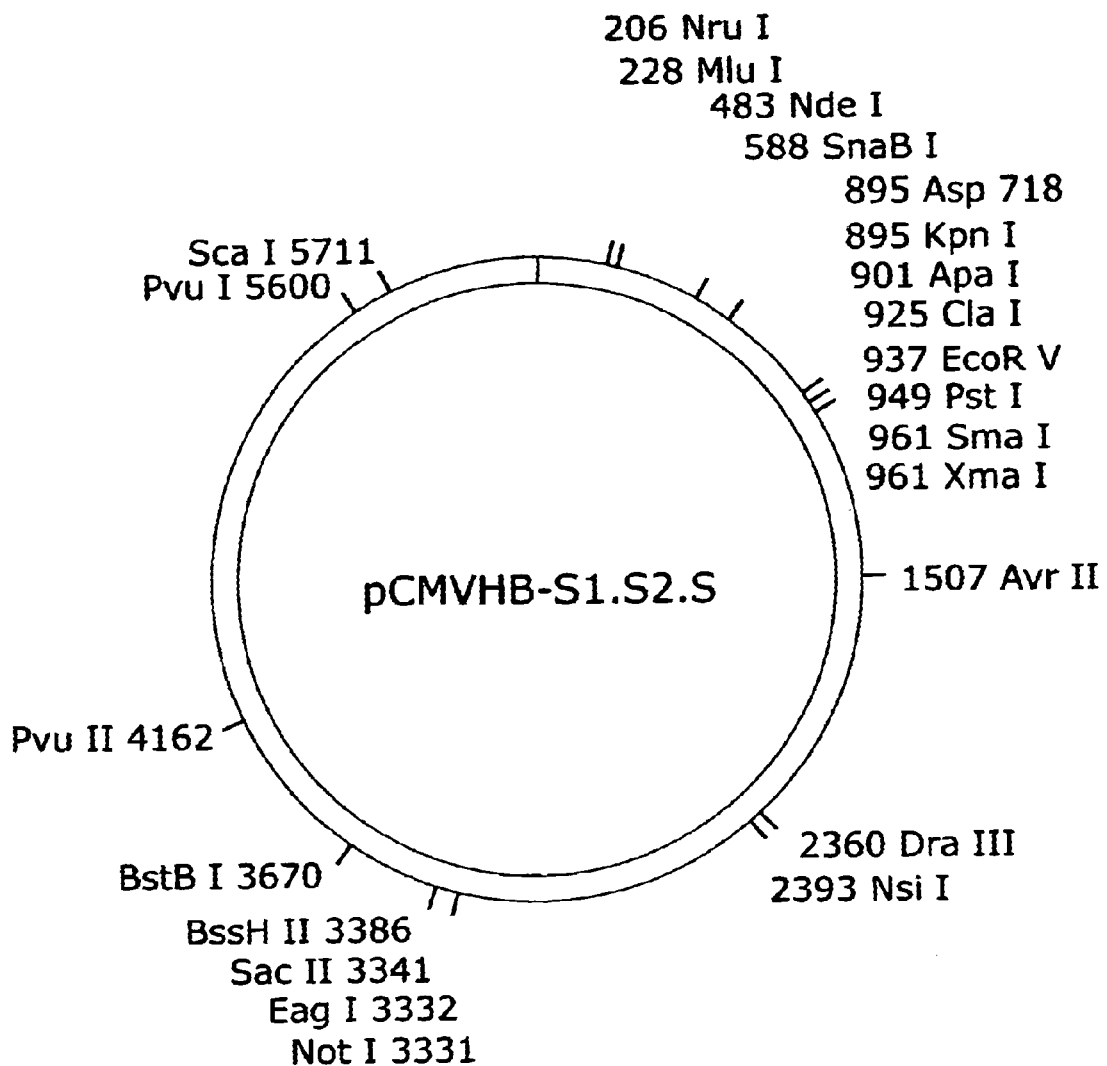
Figure 5:
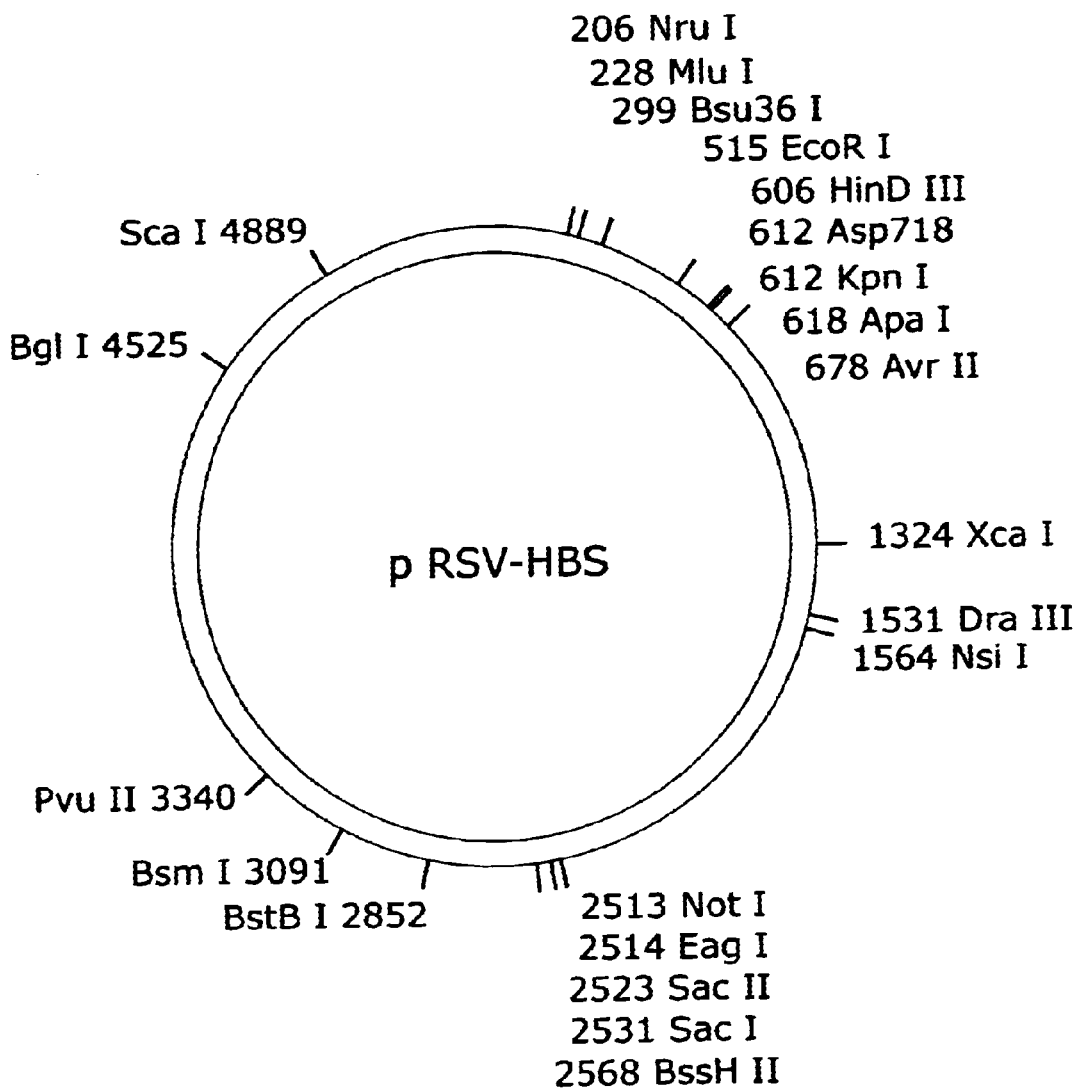

Comparison of the Responses of Mice and Rabbits to Plasmids Carrying Different Promoters and Envelope Genes for the HBV Virus Four plasmids were constructed allowing the expression of one, two or three envelope proteins for the HBV virus. In three of the constructions (pCMVBH-S, pCMVHB-S2.S, pCMVHB-S1.S2.S) the genes coding for the HBV virus envelope proteins are put under transcriptional control of the promoter of the CMV virus precursor genes (FIG. 1, FIGS. 2A to 2C, FIGS. 3 and 4). The fourth plasmid (pHBV-S1.S2.S) uses the promoter for the HBV virus surface genes contained in the pre-Si region of this virus (Cattaneo et al. (1983) Nature, 305, 336) (FIG. 2D) as a transcriptional controlling element. In the four constructions, the polyadenylation signal used is contained in the HBV sequences present in 3' of the S gene.

1. In Vitro Control of the Vector Efficiency.

Figure 6:
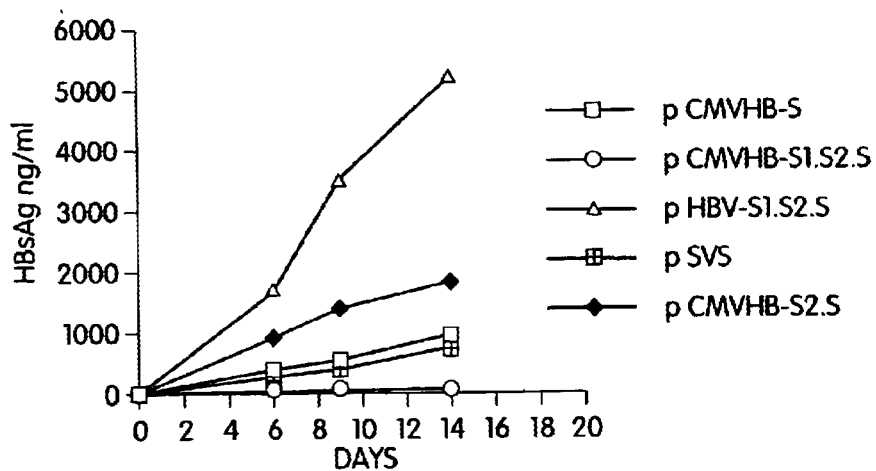
FIG. 6 illustrates the secretion of antigenic HBs particles (HBs Ag) in ng/ml (ordinates) as a function of the number of days (abscissa) for cells carrying the pCMVHB-S, pCMVHB-S1.S2.S, pHBV-S1.S2.S, pSVS or pCMVHB-S2.S plasmids.

To control the efficiency of these vectors in vitro in eucaryote cells, mouse fibroblasts or myoblasts were transfected. A plasmid expressing the three envelope proteins under control of the SV40 promoter (pSVS) was used as a control (Michel et al. 1984, Proc. Natl. Acad. Sci. USA, 81, 7708–7712)). FIG. 6 illustrates the secretion kinetics of the HBs particles in the culture supernatants. The low antigen levels produced by transfection of the pCMVHB-S1.S2.S vector are compatible with a large degree of synthesis of the large envelope protein starting from the CMV promoter. This protein being myristilised in its amino terminal region, is retained in the endoplasmic reticulum (Ganem, (1991), Current Topics in Microbiology and Immunology, 168, 61–83). Retention in the cell of proteins carrying the pre-S1 determinants was confirmed by immunofluorescence.

Figure 7A:
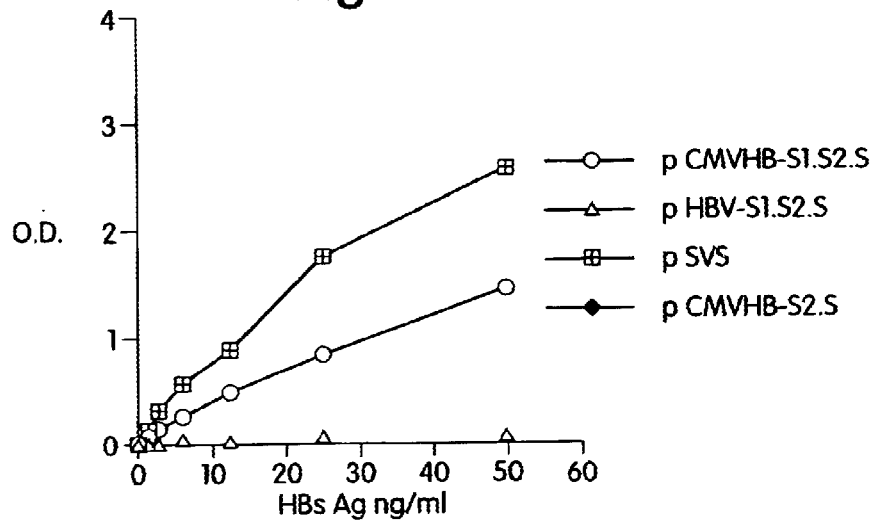
FIGS. 7A and 7B illustrate the determination on some particles in FIG. 6 of the presence of the preS$_1$ and PreS$_2$ antigens using respectively anti-preS₁ and anti-preS₂ antibodies. The formation of antibody-antigen complexes is shown by the optical density (ordinates), as a function of antigen concentration.
Figure 7B:
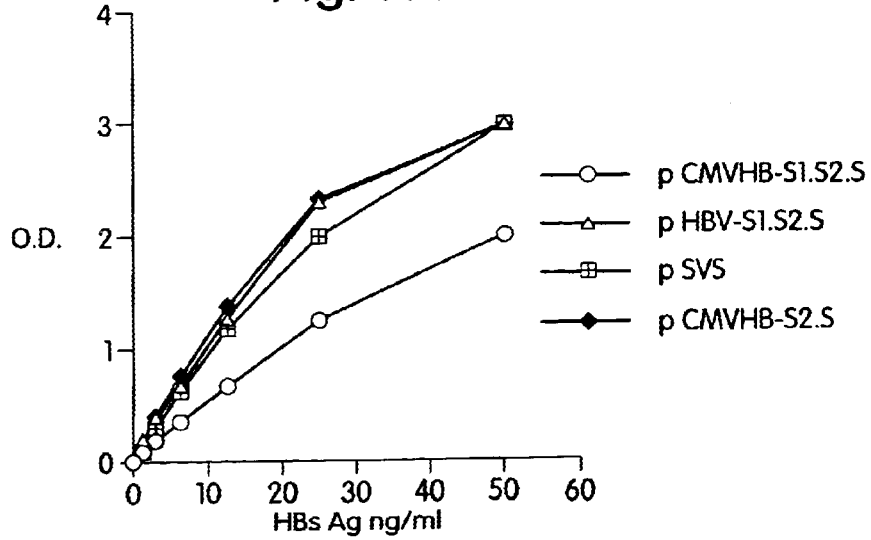
Figure 8A:
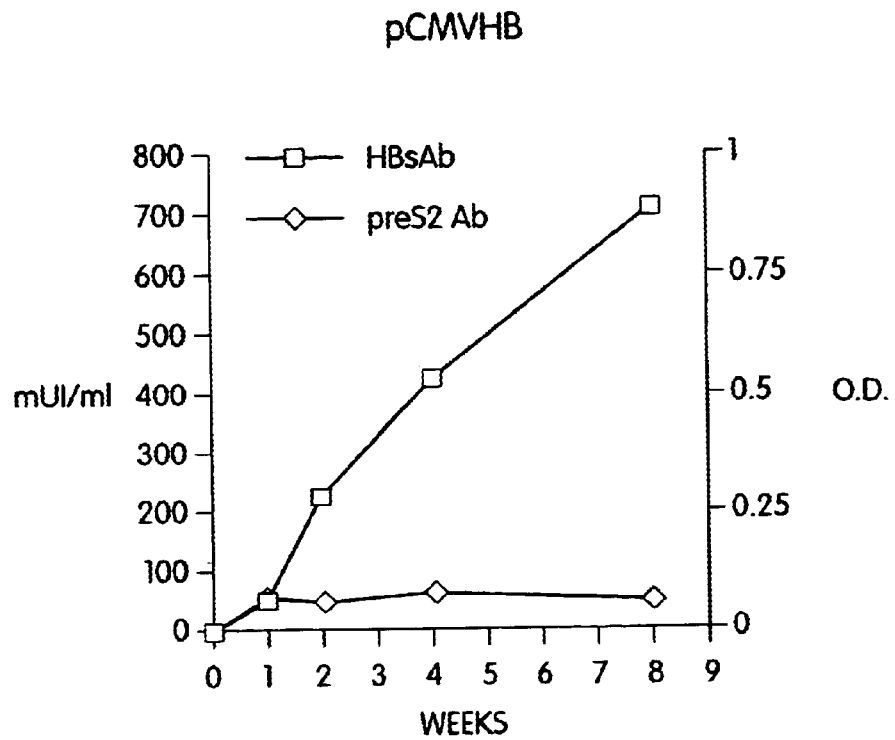
FIGS. 8A to 8D represent the anti-HBS responses (HBS Ab as ordinate, expressed as mUI/ml) and anti-preS2 (preS2 Ab as ordinate, expressed in O.D.) of mice vaccinated by pCMVHB-S (8A), pCMVHB-S2.S (8B), pCMVHB-S1.S2.S (8C) and pHBV-S1.S2.S (8D), respectively.
Figure 8B:
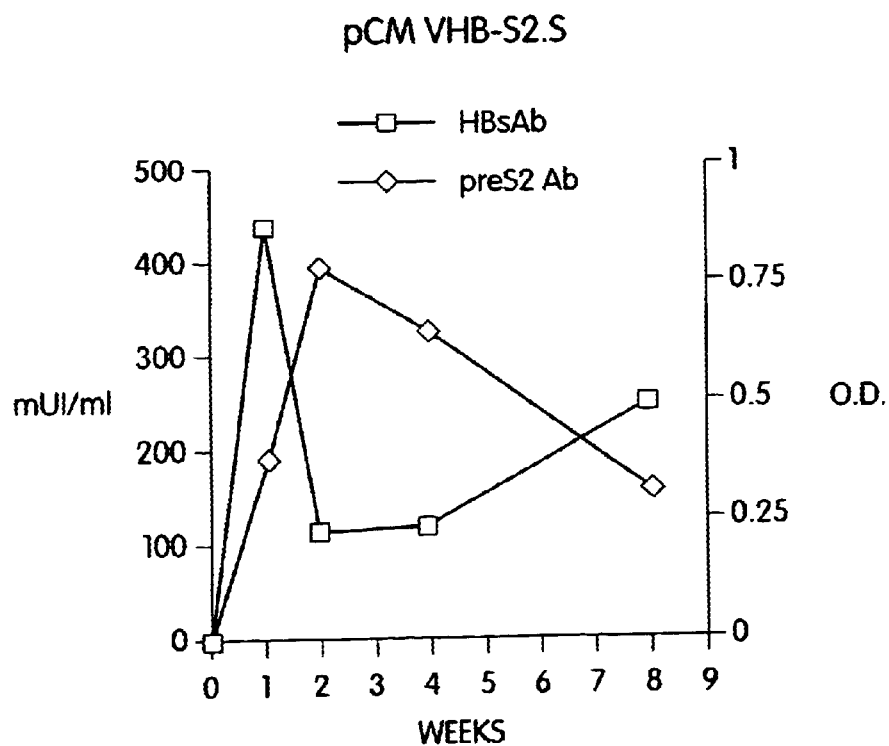
Figure 8C:
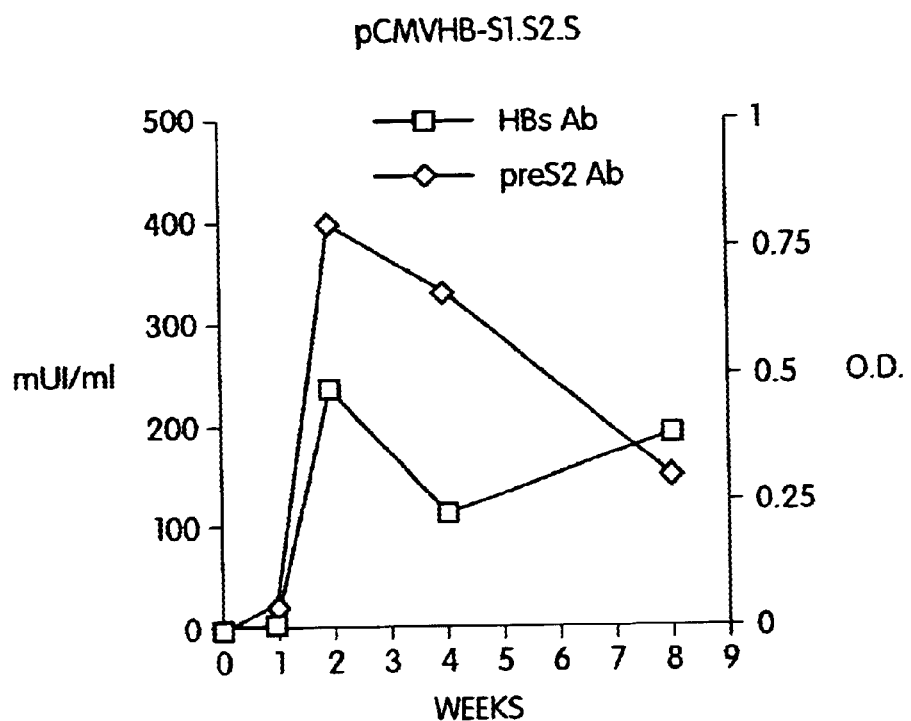
Figure 8D:
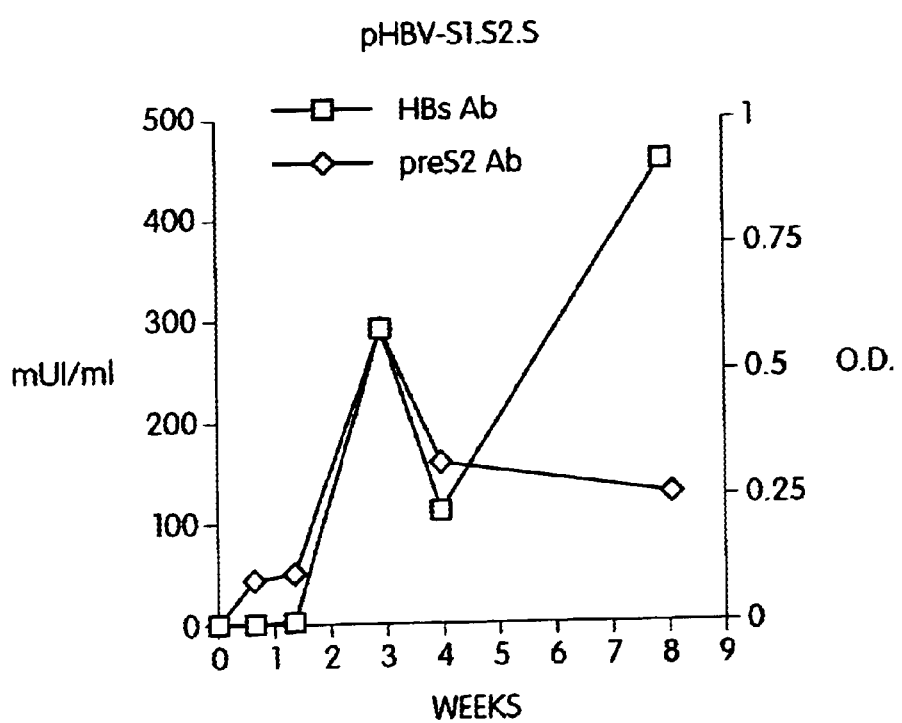

The composition of the secreted particles was analyzed in an ELISA sandwich system using as capture antibodies a monoclonal mouse antibody specific to the pre-S1 (FIG. 7A) or pre-S2 (FIG. 7B) determinants as capture antibodies and rabbit anti-HBs polyclonal serum as second antibodies. These experiments show that the AgHBs particles produced starting from pCMVHB-S1.S2.S vector carry pre-S1 and Pre-S2 determinants showing the presence of the large and medium envelope proteins of the HBV virus. Particles secreted after the transfection of the pCMVHB-S2.S and pHBV-S1.S2.S vectors carry, in addition to the HBs determinants, pre-S2 determinants characteristic of the medium envelope proteins.

2) DNA Inoculation

DNA purified on a Quiagen column was injected by an intramuscular path in a single injection of 100 μg (50 μg/leg) in the anterior tibia muscle of mice C57/BL6 (8 mice per group). Five days prior to the injection, the muscle was pretreated with cardiotoxin in order to induce degeneration followed by regeneration of the muscles cells thus favoring the DNA capture by these cells.

The DNA injection experiments were also carried out for rabbits. In this case, pCMVHB-S DNA was administered into normal muscle without degeneration, either by using an injection gun without needle called Biojector$^R$, or by conventional syringes fitted with needles.

3) Anti-Hbs Responses for Mice Vaccinated With DNA

An anti-HBs antibody response is induced by a single injection of one or other of the four plasmids used.

The antibody response was analyzed using a commercial anti-HBs antibodies detection kit (Monolisa anti-HBs, Diagnostic Pasteur). Anti-preS2 antibodies are detected by an ELISA system using, on the solid phase, a peptide from the pre-S2 (AA 120–145) region on the solid phase corresponding to a B major epitope carried by this area (Neuarth et al., (1985), Nature, 315, 154).

FIGS. 8A to 8D illustrate the anti-HBs (HBs-Ab) response kinetics expressed in milli-international units/ml and the anti-pre-S2 response (pres2Ab) determined as optical density (492 nm) for 1/100 diluted serums. Detection was carried out using a mouse anti-immunoglobulin antibody (IgG) coded with peroxidase.

The injection of the pCMVHB-S plasmid (FIG. 8A) induces a constant anti-HBs antibody synthesis. Seroconversion was observed in 100% of mice from one week after the injection with an antibody average level of 48 mUI/ml (from 12 to 84 mUI/ml, standard deviation (SD)=28), which is 4 to 5 times superior to the threshold required in man to provide protection (10 mUI/ml).

The induced response for a single injection of pCMVHB-S2.S plasmid (FIG. 8B) is characterized by the very early apparition of anti-HBs antibodies. These antibodies reach an average level of 439 mUI/ml (from 104 to 835 mUI/ml; SD 227) at one week then reduce before increasing again to reach the initial level at 13 weeks. The significance of this antibody peak will be discussed later. A peak for anti-pre-S2 IgG antibodies is observed at two weeks.

The appearance of anti-HBs antibodies induced by injection of pCMVHBV-S1.S2.S plasmids (FIG. 8C) and pHBV-S1.S2.S (FIG. 8D) is slightly delayed as the mice only seroconvert to 100% after two weeks. The seroconversion profile is identical, it is characterized by an initial response which is specific to the pre-S2 antigen followed by an anti-HBs response which gradually increases to reach a level of 488 mUI/ml (from 91 to 1034 mUI/ml; SD=552) (pCMVHB-S1.S2.S) and 1725 mUI/ml (from 143 to 6037 mUI/ml; SD=1808) (pHBV-S1.S2.S) at 13 weeks.

4) Anti-HBS Response of Rabbits Injected With DNA

Results presented in tables III and IV show that the antibody levels detected at 8 weeks in rabbits immunized using the Biojector are significantly higher than those obtained by a DNA injection by needle.

5) Qualitative Analysis of the Humoral Response

ELISA systems applied to the solid phase of the HBs antigens of varying composition with respect to the determinants presented on the solid phase and using mouse antibodies specific to IgM or IgG as second antibodies gave a qualitative analysis of the antibody response that was achieved.

In all cases, the single injection of DNA in mice is characterized by the early appearance of AgHBs specific IgM followed immediately by conversion to IgG isotype antibodies which is characteristic of the memory response induced by the auxiliary T cells. The antibody response to the DNA injection is characterized by its prematurity. Indeed, seroconversion is achieved 8 to 15 days after the injection depending on the DNA type used and in all cases the plateau is achieved in four weeks and maintained constantly over a period of 12 weeks.

The use of the heterologous sub-type HBs antigens (ad) fixed on ELISA plates allows the formation/detection of the presence, in the serum of immunized mice, of antibodies specific to the anti-a group, and by difference in reactivity with respect to AgHBs of the same sub-type (ay), of antibodies specific to the anti-y sub-type. The presence of antibodies specific to determinants of the AgHBs group is very important as the former are capable of giving protection against the heterologous sub-type virus during virulent tests in chimpanzees (Szmuness et al. (1982) N. Engl. J. Med. 307, 1481–1486).

Figure 9:
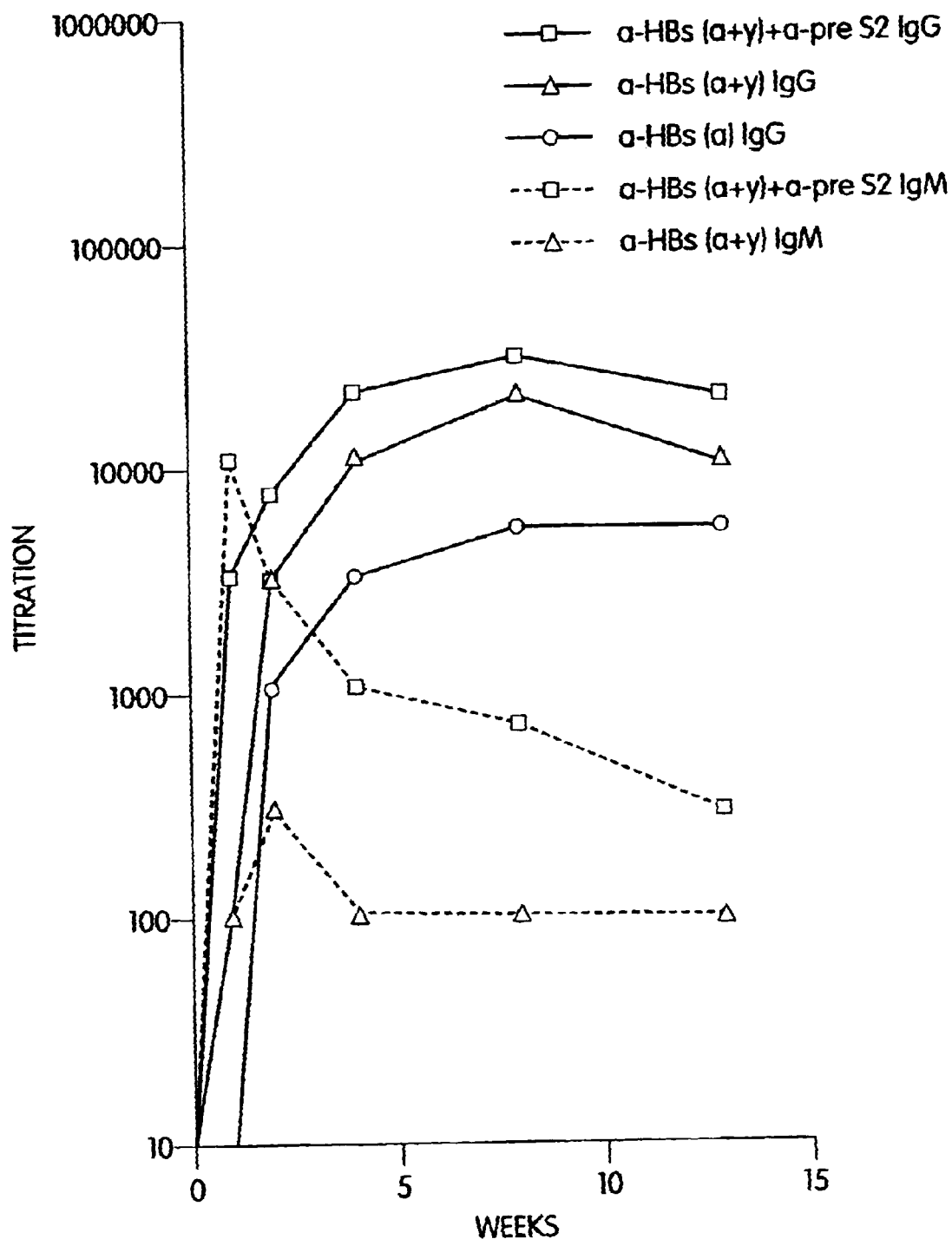
FIG. 9 illustrates the antibody response, IgG and IgM immunoglobulins (titre as ordinates), of a mouse vaccinated by pCMVHB-S2.S as a function of the number of weeks (abscissa).
Figure 10A:
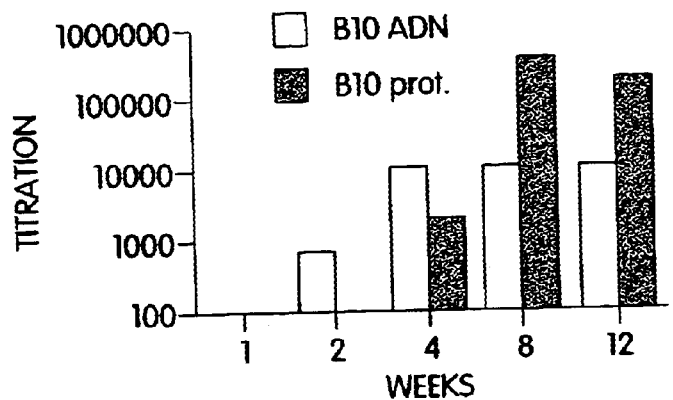
FIGS. 10A to 10C represent the anti-group and anti-subtype ay responses induced by DNA from pCMV-S (DNA) or from the HBS antigen (prot), respectively in mice B10 (10A), B10S (10B) and B10M (10C).
Figure 10B:
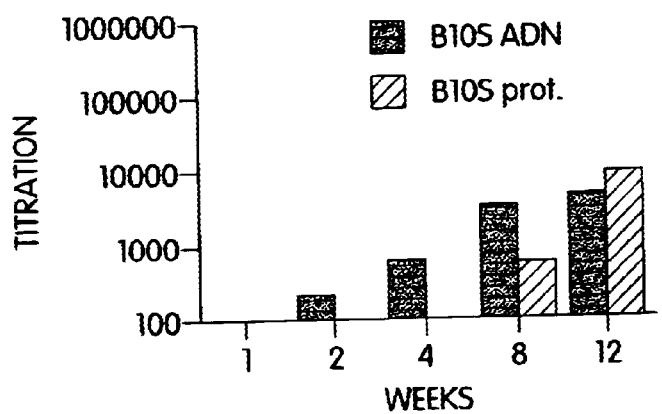
Figure 10C:
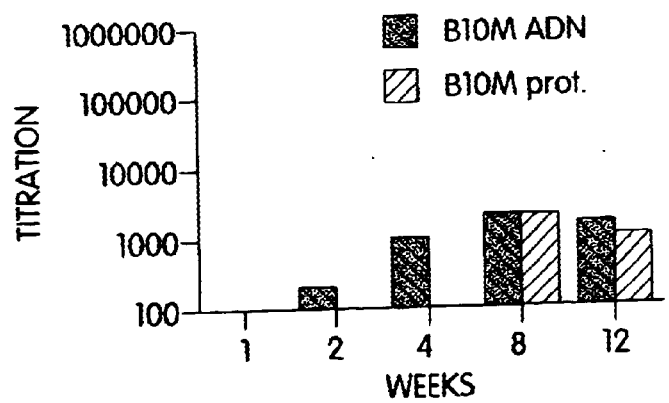
Figure 10D:
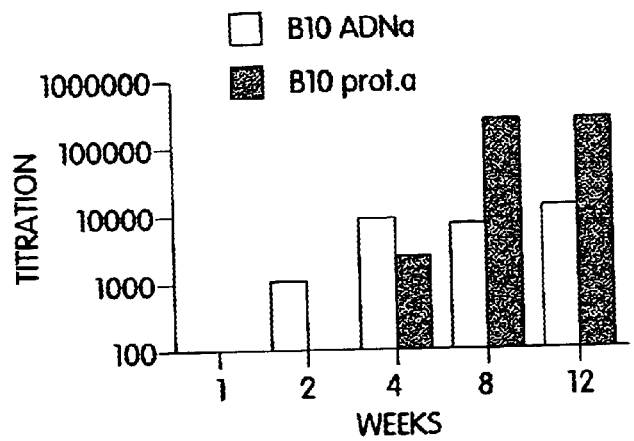
FIGS. 10D to 10F represent the antigroup responses induced by DNA from pCMV-S (DNA) or from the HBS antigens (prot), respectively in mice B10 (10D), BLOS (10E) and BLOM (10F).
Figure 10E:
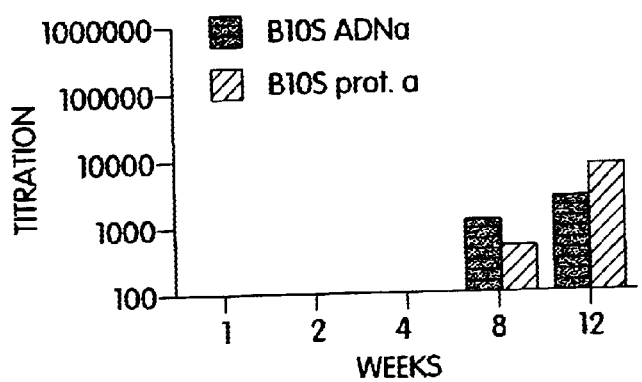
Figure 10F:
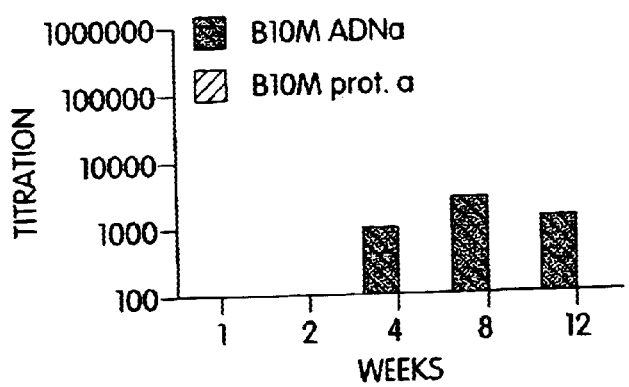
Figure 11:
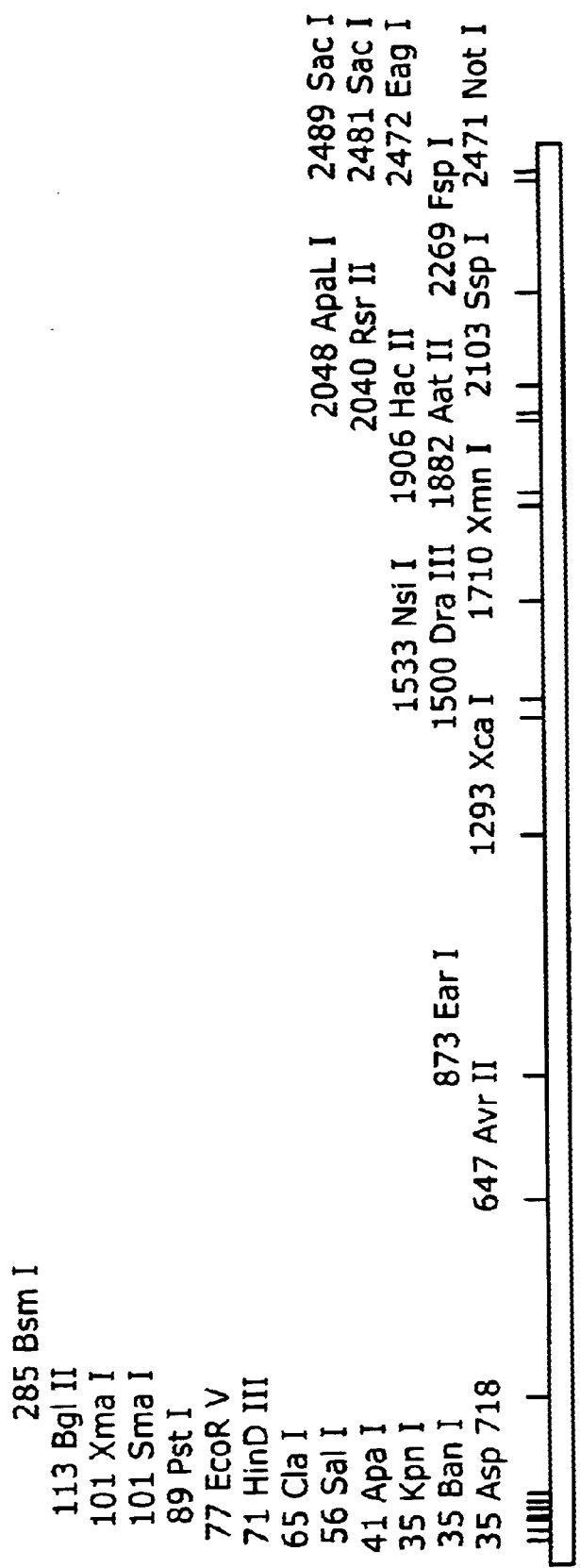
FIG. 11 represents a linear restriction map for the pBS-SKT-S1.S2.S plasmid.

Analysis of the response induced by the pCMV-S2.S vector shows that it has a remarkable similarity with the one which can be observed in man during infection. It is characterized by an extremely early (8 days) peak for IgM which is specific to the pre-S2 region immediately followed by conversion to anti-pre-S2 IgG (FIG. 9). This response is followed by the appearance of IgM then IgG anti-HBs antibodies. The anti-HBs antibody production is constant and reaches a maximum after 4 weeks. At 13 weeks IgG anti-HBS and anti-pre-S2 remain at a constant level.

The anti-sub-group (y) response precedes that of the anti-group response (a) in the same way as that described for the vaccination with the recombinant vaccine (Tron et al., (J. Infect. Dis. 160, 199–204).

The response obtained with the three other DNA vaccines illustrates the commutation of class IgM→IgG which is characteristic of the secondary response. The response being first of all directed against the sub-type before being against the AgHBs group determinants.

The long term response which was studied for pCMVHB-S DNA shows that the antibody peak is reached within 3 months and this remains at a constant level 6 months later (Table V).

6. Genetic Vaccine and Non-response

The high number of non-responders to the classical vaccine (2.5 to 5%) remains a major problem for vaccination against hepatitis B. It has been possible to correlate the non-response in man to certain HLA types (Krustall et al., (1992) J. Exp. Med. 175, 495–502) and to a defect in the antigen presentation or stimulation of the auxiliary T cells.

To study the possible impact of the genetic vaccination on the AgHBs non-response, a range of mice strains were used for which the response to various HBV virus envelope proteins is controlled genetically and has been well characterized by Millich et al. (1986 J. Immunol. 137, 315). The PCMVHB-S construction previously described was injected into B10 ($H-2^b$) B10.S ($H-2^s$) and B10.M ($H-2^f$) mice muscles.

The B10 strain responds to the three virus envelope proteins, the B10.S strain does not respond to AgHBs but this non-response can be overcome by immunization with HBsAg antigens which are carrying pre-S2 determinants. The B10M strain is totally non-responsive to both HBs and pre-S2 antigens. A response for the latter strain can be achieved by immunization using AgHBs carrying pre-Si determinants.

The mice immunized by the DNA received a single injection (100 μg) in the regenerating muscle. Control mice were injected with two intraperitonal injections of protein at an interval of one month, the first of 2 μg AgHBs to which the complete Freund additive (CFA) was added and the second of 2 μg AgHBs to which the incomplete Freund additive (IFA) was added.

The results obtained for pCMVHB-S are illustrated by FIGS. 10A to 10F.

In the B10 strain (good responder) the DNA induced response is earlier than that induced by the protein after a single injection.

The appearance of anti-HBs antibodies sub-type specific then group specific after immunization with pCMVHB-S DNA was observed in the B10S strain (non-responder to AgHBS in the absence of pre-S2). Group specific anti-HBs antibodies are observed in HBs protein immunized mice only after the second injection.

A group and sub-type specific anti-HBs response is obtained for DNA immunization of strain B10M (non-responder to AgHBs in absence of pre-S1) whereas only a sub-type specific response is induced by the protein with two injections being required.

The response induced by the three vector types is compared in the three mice strains.

CONCLUSIONS

It is generally thought that the humoral response to HBs antigens is sufficient by itself to give protection. The presence of antibodies directed against other determinants (pre-S1 and pre-S2) carried by the virus envelope proteins, themselves protectors, could improve the response quality. The experiments reported here as a whole illustrates that the humoral response induced by the genetic anti-hepatitis B vaccination is greater in several fields than that which can be achieved for the classical vaccination.

In terms of seroconversion levels: the 100% level is obtained, after only one injection, from day 8 for mice immunized with pCMV-HBS DNA and pCMVHB-S2.S.

In terms of response level: the 10 mUI/ml threshold level, considered sufficient to give protection in man, is always greatly exceeded.

In terms of the speed of response: in 8 days a very high level of anti-pre-S2 antibodies is obtained for the pCMVHB-S2.S vector and it is known that the former are capable of giving protection by themselves (Itoh et al., (1986) Proc. Natl. Acad. Sci. USA 83, 9174–9178).

In terms of response stability: anti-HBs anti-bodies remain constant at a high level for more than 6 months.

In terms of response quality: type IgG antibodies characteristic of a response which is dependent on the auxiliary T cells and therefore on a memory response are obtained.

In terms of anti-viral activity: the antibodies are specific to the viral sub-type but especially group specific and therefore susceptible to giving a cross protection.

In terms of biological significance: the response profile obtained by pCMVHB-S2.S immunization mimes totally that which is observed in man after a resolved viral infection.

Deposits: Nucleotide plasmid vectors pCMV/HBS, pRSV/HBS, and pCMV/HB-S1.S2.S, pHBV-S1.S2.S, and pCMVHB-S2.S were deposited on Oct. 21, 1993 with the Collection Nationale des Cultures des Micro-organismes de l'Institut Pasteur (CNCM) under accession numbers I-1370, I-1371, I-1411, I-1409, and I-1410, respectively. Applicants' assignee, the University of Ottawa, represents that the CNCM is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited vector, and in any case, for a period of at least thirty (30) years after the date of deposit or for the enforceable life of the patent, whichever period is longer. Applicants acknowledge their duty to replace the deposit should the depository be unable to furnish a sample when requested due to the condition of the deposit.

TABLE I

Induction of antibodies against the hepatitis B surface antigen

| Description | Number of mice | Level of antibodies against hepatitis B surface antigen in the serum (mIU/ml) Before DNA injection | 15 days after DNA injection | 35 days after DNA injection |
|---|---|---|---|---|
| DNA injected 1 day after marcaine treatment | 5 | 0 | average: 56 from 5 to >140 | average: 59 |
| DNA injected 5 days after marcaine treatment | 5 | 0 | average: 71 from 21 to >108 | average: 47 |

TABLE II

| Group | Luciferase RLU/sec/muscle (Average ± SEM) RLU = Relative Light Unit | Percentage relative to the control |
|---|---|---|
| Control | 43 082 ± 5 419 | 100% |
| 4× Dogs | 28 ± 7 | 0.06% |
| DOGS - Spermidine | 50 ± 23 | 0.12% |
| PEG-DOGS | 0 ± 0 | 0.00% |

TABLE III

Immunization with the Biojector ®

| pCMV-HB.S N° | 0 weeks | 2 weeks | 8 weeks |
|---|---|---|---|
| 2.1 | 0 | 517 | 380 |
| 2.2 | 0 | 374 | 322 |
| 3.1 | 0 | 258 | 418 |
| 4.1 | 0 | 400 | 4045 |
| 4.2 | 0 | 88 | 86 |
| 4.3 | 0 | 314 | 420 |
| 6.1 | 0 | 415 | 1001 |
| 6.2 | 0 | 1543 | 3517 |
| 6.3 | 0 | 1181 | 141 |
| Average | 0 | 566 mUI/ml | 1148 mUI/ml |
| SD | 0 | 476 | 1521 |
| SEM | 0 | 159 | 507 |
| N | 9 | 9 | 9 |
| CV |  | 84% | 133% |

TABLE IV

Immunization by injection using a needle

| pCMV-HB.S N° | 0 weeks | 2 weeks | 8 weeks |
|---|---|---|---|
| 1.1 | 1 | 0 | 1 |
| 5.1 | 0 | 287 | 186 |
| 5.2 | 0 | 162 | 798 |
| 5.3 | 0 | 305 | 203 |
| 7.1 | 0 | 86 | 175 |
| 7.2 | 0 | 1108 | dead |
| Average | 0 | 325 mUI/ml | 273 mUI/ml |
| SD | 0 | 401 | 305 |
| SEM | 0 | 164 | 136 |
| N | 6 | 6 | 5 |
| CV | 245% | 124% | 112% |

TABLE V

Long term response of a mouse vaccinated with pCMVHB-S

| | 1 month | 2 months | 3 months | 6 months |
|---|---|---|---|---|
| a-HBs titre in mUI/ml | 227 | 662 | 1299 | 1082 |
| a-HBs ELISA titre | $3.5 \times 10^{-4}$ | $5 \times 10^{-4}$ | $8.5 \times 10^{-4}$ | $9 \times 10^{-4}$ |

What is claimed is:

1. A method of inducing an immunogenic response in a subject comprising administering a nucleotide plasmid vector, wherein the vector includes a gene coding for a surface antigen protein derived from hepatitis B virus and a promoter for the expression of the gene in the subject.

2. The method of claim 1, wherein administration of said vector is conducted at least 5 days after administration of at least one substance capable of inducing a coagulating necrosis of muscle fibers and wherein said administration of said vector and said substance is about in the same area.

3. The method of claim 2, wherein said substance is bupivacaine.

4. The method of claim 3, wherein the vector is administered at least 7 days after the administration of bupivacaine.

5. The method of one of claims 1 to 4, wherein the administration is carried out by intramuscular injection.

6. The method according to claim 5, wherein the intramuscular injection is carried out using a liquid jet gun.

7. The method of claim 1, wherein the plasmid vector is administered with a vaccine adjuvant.

8. The method of claim 1, wherein the gene encodes a protein selected from the group consisting of major/small envelope protein (S), middle envelope protein ($S_{2-}$-S), and large envelope protein ($S_1$-$S_{2-}$-S).

9. The method of claim 8, wherein the gene encodes the S protein.

10. The method of claim 1, wherein the promoter is a viral promoter.

11. The method of claim 10, wherein the promoter is a cytomegalovirus promoter.

12. The method of claim 10, wherein the promoter is a hepatitis B virus promoter.

13. The method of claim 1, wherein the promoter is a mammalian promoter.

14. The method of claim 1, wherein the promoter is endogenous to hepatitis B virus.

15. A vaccine for protecting a mammal against hepatitis B virus, comprising:

a nucleotide plasmid vector, wherein the vector includes a gene coding for a surface antigen protein derived from hepatitis B virus, and a promoter for the expression of the gene in the mammal, and a vaccine adjuvant.

16. The vaccine of claim 15, further comprising a non-lipid substance capable of inducing a coagulating necrosis of the muscle fibers.

17. The vaccine of claim 16, wherein the non-lipid substance is bupivacaine.

18. The vaccine of claim 15, wherein the gene encodes a protein selected from the group consisting of major/small envelope protein (S), middle envelope protein ($S_{2-}$-S), and large envelope protein ($S_1$-$S_{2-}$-S).

19. The vaccine of claim 18, wherein the gene encodes the S protein.

20. The vaccine of claim 15, wherein the promoter is a viral promoter.

21. The vaccine of claim 20, wherein the promoter is a cytomegalovirus promoter.

22. The vaccine of claim 20, wherein the promoter is a hepatitis B virus promoter.

23. The vaccine of claim 15, wherein the is a mammalian promoter.

24. The vaccine of claim 15, wherein the promoter is endogenous to the hepatitis B virus.

25. The vaccine of claim 15, wherein the nucleotide vector is pCMV-HB-S1.S.S deposited with the CNCM under No. I-1411.

26. The vaccine of claim 15, wherein the nucleotide vector is pCMV-HB-S2.S deposited with the CNCM under No. I-1410.

27. The vaccine of claim 15, wherein the nucleotide vector is pRSV-HBS deposited with the No. I-1371 with the CNCM on Oct. 21, 1993.

28. The vaccine of claim 15, wherein the nucleotide vector is pHBV-S1.S2.S deposited with the CNCM under No. I-1409.

* * * * *